United States Patent [19]
Herrmann et al.

[11] Patent Number: 5,861,241
[45] Date of Patent: Jan. 19, 1999

[54] MONOCLONAL ANTIBODIES FOR DETECTING NORWALK VIRUS

[75] Inventors: John E. Herrmann, Northboro; Neil R. Blacklow, Weston, both of Mass.

[73] Assignee: University of Massachusetts, Boston, Mass.

[21] Appl. No.: 689,890

[22] Filed: Aug. 15, 1996

Related U.S. Application Data

[60] Provisional application No. 60/002,462 Aug. 16, 1995.
[51] Int. Cl. [6] .............................. C12Q 1/70; C07K 16/00
[52] U.S. Cl. ........................ 435/5; 530/387.1; 530/387.2; 530/388.1
[58] Field of Search .............................. 435/5; 530/388.1, 530/387.1, 387.2; 424/184.1

[56] References Cited

U.S. PATENT DOCUMENTS 5,559,014  9/1996  Estes et al. ............................. 435/91.2

FOREIGN PATENT DOCUMENTS

PCT/US95/13215  3/1996  WIPO .

OTHER PUBLICATIONS

Graham et al., "Norwalk Virus . . . in Improved Assays", *The Journal of Infectious Diseases*, 170:34–43, (1994).
Green et al., "Comparison of the Reactivities . . . Epidemiologic Observations", *Journal of Clinical Microbiology*, 31:2185–2191, (1993).
Herrmann et al., "Monoclonal Antibodies . . . Antigen in Stools", *Journal of Clinical Microbiology*, 33:2155–2513, (1995).
Jiang et al., "Expression, Self–Assembly . . . Capsid Protein", *Journal of Virology*, 66:6527–6532, (1992).
Okhuysen et al., "Viral Shedding and Fecal . . . Norwalk Virus Infection", *The Journal of Infectious Diseases*, 171:566–569, (1995).

*Primary Examiner*—Michael P. Woodward
*Assistant Examiner*—Brenda Glass Brumback
*Attorney, Agent, or Firm*—Fish & Richardson P.C.

[57] ABSTRACT

Monoclonal antibodies and their use in assays to determine the presence of Norwalk virus, Norwalk virus particles, or Norwalk virus-specific IgM, in a biological sample. One assay includes the steps of contacting the sample with a monoclonal antibody that specifically binds to Norwalk virus particles in human stool; reacting the sample and the antibody for a time and under conditions that allow the formation of an immunocomplex between the antibody and any Norwalk virus in the sample; and detecting the immunocomplex, the presence of the immunocomplex indicating the presence of human Norwalk virus in the sample. Another assay is an IgM capture antibody immunoassay.

12 Claims, 2 Drawing Sheets

MONOCLONAL ANTIBODIES FOR DETECTING NORWALK VIRUS

CROSS-REFERENCE TO RELATED APPLICATION

This application claims benefit from U.S. Provisional Patent Application Serial No. 60/002462, filed on Aug. 16, 1995.

BACKGORUND OF THE INVENTION

This invention relates to methods of detecting Norwalk virus and Norwalk virus-specific IgM with monoclonal antibodies.

Norwalk virus, the prototype calicivirus, is a major cause of outbreaks of gastroenteritis, affecting primarily older children and adults. Although Norwalk virus has been known since its first outbreak in Norwalk, Ohio in 1968, viral particles were not visualized until 1972. The 27 nm diameter particles were first observed in a stool sample by immune electron microscopy using serum from a symptomatic patient. Norwalk virus has not been serially propagated in cell cultures, which has inhibited the study and diagnosis of this virus and its antigens. Instead, diagnosis is accomplished by PCR, ELISA, antigen detection, electron microscopy, or by serologic methods.

Diagnosis of Norwalk virus infections by serological means or by antigen detection in the past has relied on use of clinical materials, e.g., human serum, obtained from volunteers infected with the virus. The Norwalk virus genome has been cloned and a Norwalk virus capsid protein has been expressed as described in Jiang et al., *Science*, 250:1580–1583, 1990 and Jiang et al., *J. Virol.*, 66:6527–6532, 1992. Antisera to the recombinant Norwalk virus (rNV) capsid protein have been prepared and used in an ELISA for antigen detection. The ELISA was highly specific for the prototype Norwalk virus, and showed that some virus isolates that had been previously identified as Norwalk-related viruses by tests using human reagents were distinct from prototype Norwalk virus (Graham et al., *J. Infect. Dis., 170:34–43, 1994*). However, antisera to the rNV capsid protein have not been demonstrated to react to any stool samples from naturally occurring Norwalk virus outbreaks.

Moreover, the use of IgG-based serologic methods for Norwalk virus diagnosis is limited because these methods require the use of paired acute and convalescent phase sera. If only late-stage acute serum is available, showing a clear positive increase in Norwalk virus-specific IgG may not be possible if the acute phase serum already has a high titer.

SUMMARY OF THE INVENTION

The invention features new monoclonal antibodies that specifically bind to Norwalk virus particles in stool from a human patient infected with Norwalk virus, and in particular, two new monoclonal antibodies designated herein as 1C9 and 1D8.

In another aspect, the invention generally features immunoassays to determine the presence of Norwalk virus or virus antigens, e.g., particles, in a biological sample, e.g., a stool sample, by contacting the sample with a monoclonal antibody of the invention, e.g., 1C9 or 1D8; reacting the sample and the antibody for a time and under conditions that allow the formation of an immunocomplex between the antibody and any Norwalk virus or virus antigens in the sample; and detecting the immunocomplex, the presence of the immunocomplex indicating the presence of human Norwalk virus or virus particles in the sample. The viral antigen can be, for example, the 58 KDa Norwalk virus protein described herein.

In one embodiment of this assay, the immunocomplex can be detected by a competitive immunoassay by reacting the monoclonal antibody with the sample and with a competing antigen to which the monoclonal antibody is known to specifically bind, e.g., a labeled Norwalk virus antigen or an immobilized competing antigen such as a recombinant Norwalk virus capsid protein. The competing antigen can be labeled or immobilized.

In another embodiment, the immunoassay is a sandwich immunoassay that uses a second antibody, e.g., a monoclonal antibody, that either also binds Norwalk viral particles or binds to the first monoclonal antibody, one of the two antibodies being immobilized and the other being labeled using standard techniques. In the sandwich immunoassay procedures, the Norwalk viral particle-binding antibody can be a capture antibody attached to an insoluble material, and the second Norwalk viral particle-binding antibody can be a detector or labeling antibody.

The immunoassay in another embodiment is a Norwalk virus antigen-based IgM-capture enzyme immunoassay (EIA) that uses a monoclonal antibody of the invention. This immunoassay enables the relatively early detection of Norwalk virus, and requires only one serum sample, compared to two samples (taken at about four week intervals) required for typical IgG seroconversion assays. This assay can be used to determine the presence of Norwalk virus-specific IgM in a biological sample, and includes the steps of isolating, e.g., immobilizing, IgM in the sample; contacting the isolated IgM with purified Norwalk virus or Norwalk virus particles for a time and under conditions that allow the formation of a Norwalk virus-IgM complex between any Norwalk virus-specific IgM in the sample and the purified Norwalk virus or Norwalk virus particles; contacting the Norwalk virus-IgM complex with a monoclonal antibody that specifically binds to Norwalk virus in human stool; reacting the complex and the monoclonal antibody for a time and under conditions that allow the formation of an immunocomplex between the monoclonal antibody and any Norwalk virus-IgM complexes; and detecting the immunocomplex, the presence of the immunocomplex indicating the presence of Norwalk virus-specific IgM in the sample.

In this assay, the IgM can be isolated with an anti-human IgM antibody, such as a rabbit anti-human IgM antibody.

The immunoassays can be used to determine Norwalk virus or virus particles in samples including stool, intestinal or duodenal aspirates, urine, or peritoneal, serum, blood, and lymphatic or other bodily fluids. The assays are useful for diagnosis of individual cases of Norwalk virus infection, as well as epidemiological studies of Norwalk virus outbreaks.

In another aspect, the invention features anti-idiotypic antibodies that specifically bind to the monoclonal antibodies of the invention, e.g., 1C9 or 1D8. These anti-idiotypic antibodies can be used in a vaccine suitable for administration to humans.

The invention also features immunoassay kits for detecting Norwalk virus in human biological samples, comprising one or more Norwalk virus-binding monoclonal antibodies and the means for determining binding of the antibody or antibodies to Norwalk virus or virus particles in a biological sample. In preferred embodiments, the kit includes one or both monoclonal antibodies 1C9 and 1D8, or the competing antigens described above.

By "purified" Norwalk virus or virus particles is meant virus or virus particles that are at least 60%, by weight, free from the proteins and naturally-occurring organic molecules with which they are naturally associated. Preferably, the preparation is at least 75%, more preferably at least 90%, and most preferably at least 99%, by weight, Norwalk virus or virus particles. Purified Norwalk virus particles include recombinantly produced polypeptides or peptides, e.g., Norwalk virus capsid peptides. A purified Norwalk virus or virus particles can be obtained, for example, by affinity chromatography using antibodies or monoclonal antibodies described herein, by physical purification techniques described herein, or by other standard techniques.

The term "Norwalk virus antigen," as used herein, includes antigenic proteins or polypeptides of the virus, either naturally occurring or recombinantly or synthetically produced, to which antibodies of the invention specifically bind. The term thus includes the 58 KDa Norwalk virus protein described herein. The term "virus particle" is used to describe antigenic particles to which antibodies of the invention specifically bind.

By "specifically binds" is meant an antibody which recognizes and binds Norwalk virus or Norwalk virus particles or antigens, but which does not substantially recognize and bind other molecules in a sample, e.g., a biological sample, which naturally includes Norwalk virus or virus particles.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the following detailed description, and from the claims.

DETAILED DESCRIPTION

Figure 1:
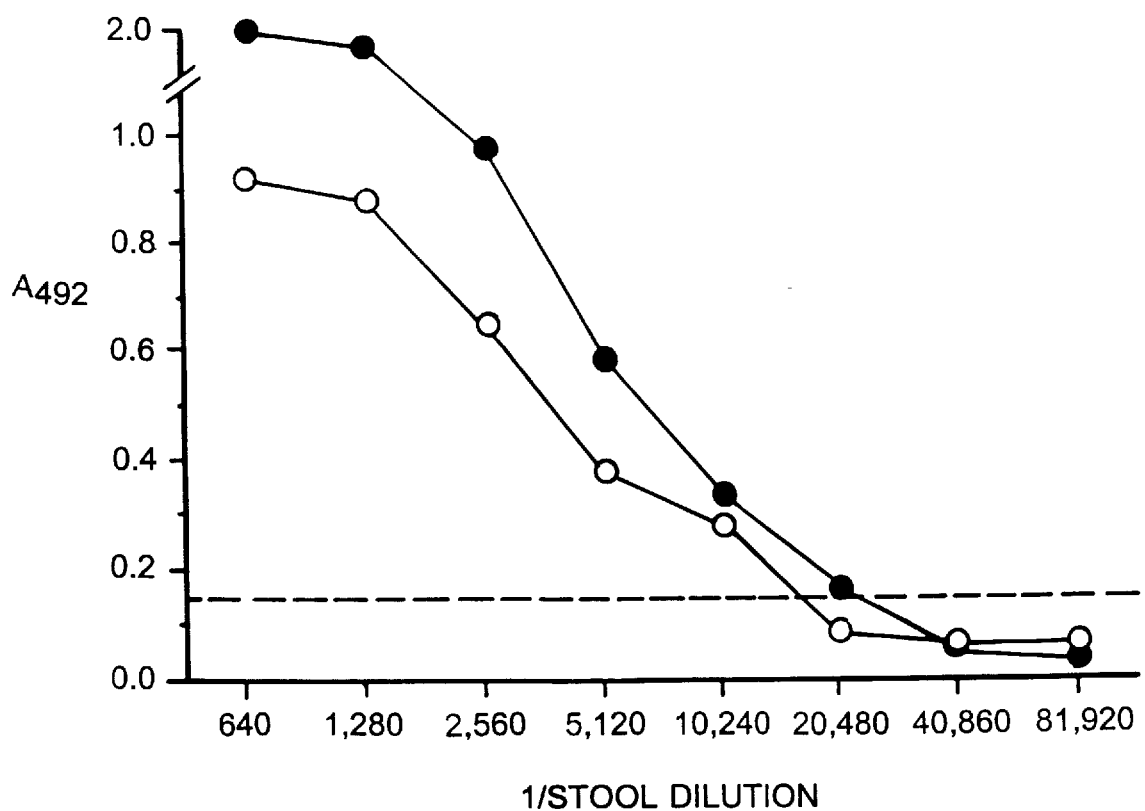
FIG. 1 is a graph showing the titration of Norwalk virus antigen in a stool specimen from a volunteer by monoclonal antibody ELISA (closed circles) and polyclonal antibody (open circles). Points above the dotted line represent positive values for the immunoassays.

Applicants have obtained monoclonal antibodies that specifically bind Norwalk viral particles derived from a human stool sample from a patient infected with the virus. These antibodies are useful in various immunoassays to detect the presence of Norwalk virus or virus particles or Norwalk virus-specific IgM in clinical samples from outbreaks of Norwalk virus infection.

Purification of Norwalk Viral Particles

Norwalk virus was obtained from the diarrheal stool of a volunteer who had been inoculated with Norwalk virus strain 8FIIa. Virus was partially purified from stool material by differential centrifugation and banding in CsCl gradients, essentially according to the procedures described by Greenberg et al., *J. Virol.*, 37:994–999, 1981. Fractions were collected, assayed for density, and tested by ELISA for Norwalk virus antigen. Fractions which had densities of 1.34 to 1.40 and showed high reactivity by ELISA as described below were pooled, dialyzed against 0.01M phosphate-buffered saline, pH 7.2, and used as virus inoculum for hybridoma production.

Hybridoma Production

Hybridomas were produced as described in Herrmann et al., *J. Clin. Microbiol.*, 33:2511–2513, 1995. BALB/c mice (eight-week-old females) were inoculated subcutaneously with 0.1 ml of stool-derived Norwalk virus emulsified in an equal volume of TiterMax adjuvant (Vaxcel, Inc., Norcross, Ga.). Mice were given a second subcutaneous inoculation three weeks later. The mice were given two more inoculations (intraperitoneal) of Norwalk virus in Freund's incomplete adjuvant, and one intraperitoneal inoculation of virus without adjuvant, all two weeks apart. Five days after the last inoculation, mouse spleens were fused to SP 2/0 myeloma cells with Kodak polyethylene glycol 1450 plus DMSO, according to the procedures described by Lane, *J. Immunol. Methods*, 181:223–228, 1985. Hybrid cells were seeded onto 24 well plates in HAT medium containing 10% Hybridoma Cloning Factor (IGEN, Inc., Rockville, Md.). After seven days, hybridomas were screened for antibodies which reacted with Norwalk virus antigen from stools obtained from volunteers.

Hybridomas that secreted such antibodies were cloned twice by use of the limiting dilution technique. Ascitic fluids for all clones were prepared in BALB/c mice. The techniques described herein can be used to obtain monoclonal antibodies that specifically bind to Norwalk virus particles form stool samples such as the particular antibodies 1C9 and 1D8 described herein.

Immunoassays

Enzyme Immunoassays of Stool Samples

Enzyme immunoassays (EIAs) were used to screen hybridoma supernatant fluids and to test virus-specific reactivity as described in Herrmann et al., *J. Clin. Microbiol.*, 33:2511–13, 1995. For these tests, stool extracts known to contain Norwalk virus antigen, and rNV capsid protein were tested by modification of an EIA for detecting Norwalk virus which used polyclonal human sera described in Herrmann et al., *J. Med. Virol.*, 17:127–133, 1985.

For the indirect EIA used to screen hybridomas, wells of polyvinyl chloride microtiter plates were coated with pre- and post-challenge sera (four-week convalescent) from a volunteer infected with Norwalk virus. The wells were coated for 24 hours at room temperature (20°–22° C.), and post-coated with 1% w/v bovine serum albumin in 0.01M phosphate-buffered saline (PBS) for 24 hours at 4° C.

Suspensions of stool-derived Norwalk virus or rNV capsid protein were added to the wells and incubated 18–24 hours at 20°–22° C. The plates were washed with PBS and 0.05 ml of hybridoma supernatant fluids diluted in 50% fetal calf serum and 50% 0.025M Tris-HCl buffer (pH 7.2) with 0.015% Tween 20, were added and incubated for 1 hour at 37° C. Peroxidase-labelled goat antibody specific for mouse IgG (Kirkegaard and Perry Laboratories, Gaithersburg, Md.), at 1 µg/mL in the Tris buffer used above, was added and incubated for 1 hour at 37° C. The plates were washed five times with PBS, soaked for 30 seconds with PBS containing 0.05% Tween 20, and washed again. Substrate for peroxidase (0.05 mL, O-phenylene-diamine-$H_2O_2$; Abbott Laboratories, North Chicago, Ill.) was added for 10 minutes, and the reaction was stopped with 0.1 mL of 1N $H_2SO_4$. Biotin/avidin labeling systems can also be used.

The absorbance of the solution was measured at 492 nm in a plate-reader spectrophotometer. After monoclonal antibodies were obtained, a direct EIA was used for testing stool samples; however, other standard immunoassays can also be used. The same monoclonal antibodies were used for coating plates and for antigen detection. The antibodies were purified from ascitic fluid by ammonium sulfate precipitation, and either used directly for coating plates or labelled with peroxidase for use as detector antibodies. The antibodies were labelled with peroxidase by the periodate method of Wilson and Nakane, "Recent developments in the periodate method of conjugating horseradish peroxidase (HRPO) to antibodies," p. 215–224. In: Knapp et al. (eds.), *Immunofluorescence and Related Staining Techniques* (Elsevier/North Holland Biomedical Press, Amsterdam, 1978).

For the EIA, wells were coated with monoclonal antibodies (2 µg/mL) for 18 to 24 hour at 20°–22° C., washed, and post coated with Superblock (Pierce Chemical Co., Rockford, Ill.) 4 to 6 hours. The plates were washed, and stool samples or controls (known positive and negative stool samples) added and incubated for 18 hours at 20°–22° C. Plates were washed, and the peroxidase conjugated antibodies added and incubated at 37° C. for 2 hours. The remaining procedures were as described for the indirect EIA. Samples were considered positive for monoclonal antibody to Norwalk virus in the screening tests, or for Norwalk virus antigen in the virus-specificity tests, if the absorbance value was both $\geq 0.1$ and three or more times the negative control (wells coated with pre-immune serum in the screening tests, and wells coated with an unrelated monoclonal antibody in the virus specificity tests).

Antigen-based IgG-capture EIA of Serum Samples

Recombinant Norwalk virus antigen-based IgM-capture enzyme immunoassays were used to test serum samples from two groups of human volunteers infected with Norwalk virus, and who had either an IgG antibody increase against recombinant NV capsid protein, or were virus positive.

Volunteer Group I samples consisted of pre-inoculation sera followed by sera collected from five days to 22 weeks post-inoculation of the 8FIIa strain of Norwalk virus (these samples were collected in the 1970s and stored at or below −20° C.). Volunteer Group II was inoculated with 8FIIa in 1995, and samples consisted of pre-inoculation sera followed by sera collected at 4, 5, 8, 14 and 21 days post-challenge. Samples from two natural Norwalk virus outbreaks were also tested. The first set of outbreak samples (Outbreak Group I) was from a Norwalk virus clam-associated outbreak of gastroenteritis in Hawaii in 1983. The second set of outbreak samples (outbreak Group II) was from an outbreak of gastroenteritis in Erie County, New York, in 1986.

Sera from volunteers challenged with Hawaii virus and sera from a Snow Mountain virus outbreak were also tested, in addition to sera from a group of normal human adult donors from a hospital blood bank and non-symptomatic children admitted to the hospital for reasons other than gastroenteritis. All sera were stored at or below −20° C.

For the IgM capture antibody ELISA, polyvinyl plates (Dynatech Laboratories, Inc., Chantilly, Va.) were coated with unlabeled rabbit anti-human IgM (Fc5µ) (Accurate Chemical, Westbury, N.Y.) at a concentration of 0.25 µg/50 µl of 0.1M PBS per well. Plates were incubated at 37° C. for 2 hours, washed three times with PBS plus 0.15% TWEEN-20™ and blocked overnight with 5.0% BSA and 0.25% Bloom 60 gelatin in PBS. The plates were washed three times and duplicate two fold serial dilutions of human serum were made in 50% fetal bovine serum (50% 0.025M Tris-HCL buffer (pH 7.2) with 0.015% TWEEN-20™), and incubated for 1 hour at 37° C.

The plates were washed five times and 50 ng of recombinant Norwalk virus (rNV) capsid antigen, in 50 µl of the Tris-HCL-FBS buffer described above, was added to each well of one of the duplicate rows. To the second row, 50 µl of Tris-HCL-FBS buffer without rNV was added.

After overnight incubation at 20°–22° C., the plates were washed five times and a combination of the two murine monoclonal antibodies 1C9 and 1D8 was added in Tris-HCL-FBS buffer to all wells and incubated at 37° C. for 1 hour. The plates were washed and peroxidase-labeled goat anti-mouse immunoglobulin G (Kirkegaard & Perry Laboratories, Inc., Gaithersburg, Md.) at 1 µg/ml in Tris HCL-FBS buffer plus 1% normal rabbit serum was added and incubated for 1 hour at 37° C. The plates were washed five times. Substrate for peroxidase (0.05 ml of O-phenylenediamine-$H_2O_2$, Abbott Laboratories, North Chicago, Ill.) was added and left for up to 10 minutes. The reaction was stopped with 0.1 ml of 1N $H_2SO_4$.

The absorbance (optical density) of the solution was measured at 492 nm ($A_{492}$) in a plate-reader spectrophotometer. The endpoint titer was defined as the highest dilution of serum giving an optical density at $A_{492}$ of greater than or equal to 0.200 units higher than the corresponding antigen deficient well. To confirm IgM specificity, IgG and IgA were removed from the Group I volunteer sera with Quik-SepIgM (Isolab Inc., Akron, Ohio) and tested in the same manner as the whole serum.

Radioimmunoprecipitation Tests

Radioimmunoprecipitation tests were done to determine the reactivity of the monoclonal antibodies with Norwalk virus capsid proteins produced in vitro. These proteins were produced from full-length open reading frame (ORF)-2 clones, which were described in Jiang et al., *J. Virol.*, 66:6527–6532, 1992, to code for the Norwalk virus capsid protein. Reverse transcriptase-PCR was used to obtain full-length ORF-2 clones from Norwalk virus RNA isolated by standard silica extraction from a fecal sample containing intact virus particles. Oligo (dT) was used for reverse transcription to produce first-strand cDNA.

Specific Norwalk virus primers were used in first found PCR reactions. PCR products were amplified using a "half-nested" approach (same 5'-end primers as in the first round, with a unique 3'-end primer, internal to the first round 3'-end primer). Second round PCR products were made blunt-ended with T4 DNA polymerase and digested with Cla I. The product (with a staggered 5'-end and a blunt 3'-end) was ligated into Cla I and Sma I-digested pBluescript KS-.

ORF-2 was expressed in vitro in a coupled transcription-translation system (Promega Corp., Madison, Wis.) and products were metabolically labeled with [$^{35}$S]-methionine. Immunoprecipitations were performed as previously described for astrovirus capsid proteins in Lewis et al., *J.Virol.*, 68:77–83, 1994.

Figures 2A, 2B:
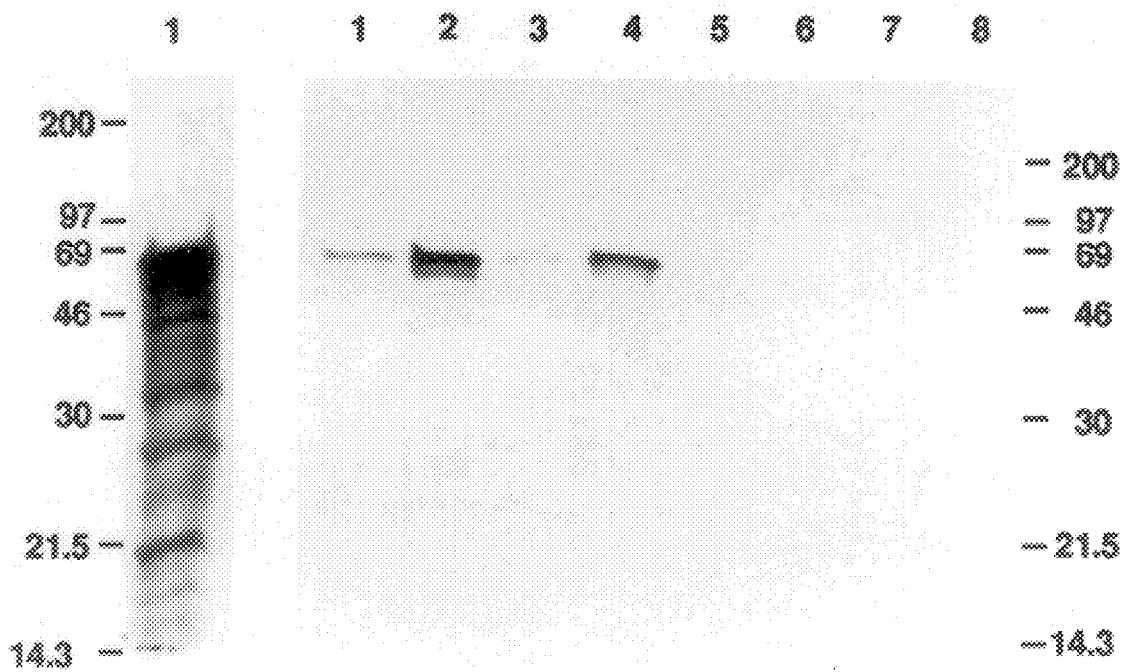
FIG. 2A is a photograph of a gel showing untreated, radiolabeled translation products of Norwalk virus ORF-2. Numbers on the left are molecular masses in kilodaltons.
FIG. 2B is a photograph of a gel showing immunoprecipitation of radiolabeled Norwalk virus ORF-2 translation products with Norwalk virus-specific monoclonal antibodies 1D8 (lane 1, 3 μL reaction product immunoprecipitated; lane 2, 15 μL) and 1C9 (lane 3, 3 μL lane 4, 15 μL) compared to immunoprecipitation with astrovirus-specific monoclonal antibody 8E7 (lane 5, 3 μl; lane 6, 15 μL ). Norwalk monoclonal antibodies 1D8 (lane 7) and 1C9 (lane 8) were also tested for reactivity with radiolabeled astrovirus ORF-2 translation products (capsid). Numbers on the right are molecular masses in kilodaltons.

The results of the immunoprecipitation studies are given in FIGS. 2A and 2B. A predominant 58 kDa band, indicative of Norwalk virus protein, was seen in crude lysates. Norwalk virus-specific proteins were immunoprecipitated with monoclonal antibodies 1D8 (lane 1, 2) and 1C9 (lane 3, 4). The predominant product seen in lanes 1 to 4 is a 58 kDa protein. An astrovirus-specific monoclonal antibody (8E7) failed to immunoprecipitate any Norwalk virus ORF-2 translation products (lane 5, 6). Conversely, Norwalk virus-specific monoclonal antibodies 1D8 and 1C9 did not immunoprecipitate any astrovirus capsid proteins (lanes 7, 8).

Testing of Monoclonal Antibodies

The selected hybridomas that produced antibodies reactive with both stool-derived Norwalk virus and rNV capsid protein were designated 1C9 and 1D8. No hybridomas were found that produced antibodies which reacted only with stool-derived virus or only with rNV capsid protein. Both antibodies were isotype IgG1. The two antibodies 1C9 and 1D8 appeared to be directed against different epitopes on the basis of blocking ELISA tests and the finding that a mixture of the two gave higher ELISA values than either one tested singly. This was confirmed by finding that only monoclonal antibody 1D8 reacted in an ELISA with a synthetic peptide to the N-terminus of the capsid. Based on these findings, a mixture of the two antibodies was used both for coating plates and as detector antibodies.

Stool samples containing other viruses were used for specificity testing of the monoclonal antibodies obtained. These include stools containing various U.K. strains of human calicivirus, and samples containing astroviruses, enteric adenoviruses, rotaviruses, Hawaii virus, Snow Mountain virus, unclassified "small round" viruses, and additional samples from Norwalk virus infected volunteers.

To determine the sensitivity of the monoclonal antibody ELISA compared to our previously developed polyclonal ELISA, a volunteer stool was diluted in PBS and tested by both immunoassays. The results are shown in FIG. 1. The monoclonal antibody ELISA showed greater reactivity (higher $A_{492}$ values) and 2-fold higher sensitivity in detecting Norwalk virus in a diluted stool specimen than the polyclonal antibody ELISA. Both of the ELISAs shown are of the direct type. The detection limit for the monoclonal antibody ELISA, as determined by end-point titration of rNV capsid antigen, was 0.05 ng/microwell or 1 ng/ml, which is suitable for methods of detecting Norwalk virus particles in clinical samples.

Detection of Norwalk Virus Infection in Human Samples

Various immunoassay formats are suitable for the Norwalk virus particle detection methods of the invention. For example, the ELISA, IgM-capture EIA, and radioimmunoprecipitation test described above can be used.

Human Stool Samples

In particular, representative types of gastroenteritis viruses in stool samples from human volunteers previously found to contain Norwalk virus by a polyclonal ELISA as described in Herrmann et al., *J. Med. Virol.*, 17:127–133, 1985, were used to test the specificity of the monoclonal antibodies for Norwalk virus in an ELISA. The results, presented in Table 1, indicate that the monoclonal antibodies did not react with any normal stool samples or with samples containing viruses other than Norwalk virus. However, the monoclonal antibodies of the invention reacted specifically to all 15 Norwalk virus samples tested that were previously found to be positive in a polyclonal antibody ELISA.

TABLE 1

| Patient group | No. of patients | No. ELISA positive |
|---|---|---|
| Volunteers inoculated with | | |
| Norwalk virus | 15 | 15 |
| Hawaii virus | 9 | 0 |
| Patients infected with | | |
| Rotavirus | 20 | 0 |
| Astrovirus | 7 | 0 |
| Enteric adenovirus | 7 | 0 |
| U.K. Calicivirus | 5 | 0 |
| Snow Mountain virus | 1 | 0 |
| "Small round virus" | 9 | 0 |
| Diarrhea of unknown etiology | 30 | 0 |
| Stools from patients without diarrhea | 25 | 0 |

The reactivity of monoclonal antibodies with Norwalk virus in stools was determined primarily with stools obtained from volunteers infected with a strain of Norwalk virus circulating in 1968 (the "prototype" virus). Sera prepared against the recombinant Norwalk virus capsid protein have been shown to be highly specific for this prototype Norwalk virus (Graham et al., *J. Infect. Dis.*, 170:34–43, 1994), and have not been shown to react with any stool samples from natural Norwalk virus outbreak stool samples.

It is believed that the monoclonal antibodies of the invention prepared against native virus from actual stool samples should be more broadly reactive than rNV capsid protein-generated antibodies with various Norwalk virus strains in naturally occurring outbreaks.

Strains from additional Norwalk virus outbreaks, especially recent ones, can be obtained and tested to determine the breadth of reactivity of the monoclonal antibodies of the invention for diagnosis of Norwalk virus gastroenteritis caused by different strains of the virus.

Human Serum Samples

All pre-challenge serum samples tested showed no detectable IgM. Norwalk virus-specific IgM was detected in nine of ten Volunteer Group I samples after virus inoculation (titers of 100 to 6400, 1/serum dilution). IgM was detected as early as nine days after inoculation, but two samples of ten were negative five days after inoculation. IgM titers less than 25 were considered negative in all tests. Samples were taken at two different times from each volunteer, ranging from 5 days to 7 weeks after inoculation for the first sample, and from 3 to 22 weeks after inoculation for the second sample.

In Volunteer Group II, all five volunteers were IgM negative before and up to five days after exposure, but all became IgM positive (1/serum dilution of 25 or higher) by eight days and were still positive 21 days after exposure. Samples were taken from each of the five volunteers at six time points: preinoculation, and 4, 5, 8, 14, and 21 days after inoculation.

In an rNV capsid antigen IgG assay, all of the subjects in volunteer Groups I and II showed Norwalk virus-specific rises in IgG titer. Sera from subjects in volunteer Group I that had IgG and IgA removed by Quik-Sep showed no significant differences in IgM antibody titers as compared with untreated sera.

Acute phase sera from the nine patients in Outbreak Group I (clam-associated outbreak in Hawaii in 1983) were collected from 6 to 8 days after onset of illness. Convalescent phase sera were collected 3 to 6 weeks post illness. All nine patients in Outbreak Group I had high IgM antibody titers in both acute (800 to 12,800) and convalescent sera (3,200 to 25,600). Four patients showed four-fold rises in IgM levels. All nine patients had high IgG titers to rNV capsid antigen and three had four-fold rises in IgG titer by EIA methods.

Outbreak Group II consisted of ten patients (gastroenteritis outbreak in Erie, N.Y. in 1986), all of whom had four-fold or greater rises in IgG antibodies to rNV capsid protein. Seven of the subjects had acute sera collected four days after a point source exposure and convalescent sera collected after two weeks post exposure. The other three subjects had acute sera collected between five and eight days post-exposure and convalescent sera collected three weeks post-exposure. All of the Outbreak Group II subjects had acute sera lacking IgM antibodies except one whose exposure had been five to eight days earlier. Six of the nine persons whose acute phase sera were IgM negative seroconverted to Norwalk virus-specific IgM by the two or three week samples. The one patient whose acute phase serum was IgM positive maintained a high IgM titer.

Three pairs of sera from subjects challenged with Hawaii virus and four pairs of sera from individuals in a Snow Mountain virus outbreak were tested for Norwalk virus-specific IgM. All seven serum pairs were Norwalk virus IgM negative in both acute and convalescent phase samples although they cross-reacted in the rNV capsid antigen IgG assay. Eighty normal sera from subjects ranging from age one to age 59 were also tested. Four of 20 children aged 1 to 4, 12 of 20 children aged 5 to 17, 15 of 20 adults aged 18 to 29, and all 20 adults aged 30 to 59 were positive for IgG-specific Norwalk antibodies at a 1:800 serum dilution. On the other hand, none of the normal sera were IgM positive at a 1:25 serum dilution for any age group.

Based on these studies, it appears that specific IgM is present only after recent exposure to Norwalk virus. The time that IgM specific antibodies can first be detected is important in defining NV outbreaks. In these studies, the earliest detection was at 5 days post inoculation, and all samples were positive by 8 or 9 days post inoculation. In Volunteer Group II, all five volunteers were negative at five days post inoculation and all were IgM-antibody positive by day eight. In outbreak Group I, all patients were highly positive for IgM by five to eight days post onset of illness. It appears from these groups that Norwalk virus-specific IgM develops by approximately eight days after virus exposure, and thus the capture IgM EIA described above is suitable for use in early detection of Norwalk virus infections.

DEPOSIT INFORMATION

The two hybridomas that produce monoclonal antibodies 1D8 and 1C9 were deposited with the American Type Culture Collection at 12301 Parklawn Drive, Rockville, Md., 20852 (U.S.A.) on Feb. 3, 1998, and have been assigned Accession Numbers HB-12465 and HB-12466, respectively.

OTHER EMBODIMENTS

Those skilled in the art will realize that known techniques can be used to raise anti-idiotypic antibodies, e.g., idiotypic antibodies that will bind to the monoclonal antibodies of the invention. Anti-Norwalk virus particle-binding antibodies can be used as immunogens to challenge a mammal according to known immunization regimens. See, e.g., Hellstrom et al., U.S. Pat. No. 4,918,164. The resulting anti-idiotypic antibodies can be applied, using standard techniques and methods, as: a) vaccines to induce an immune response resulting in protection against the development of Norwalk virus infection; b) immunotherapeutics to induce a patient's immune response to a Norwalk virus infection; c) competing antigens for use in the competitive immunoassay format described above; and d) as purification reagents to separate Norwalk virus-binding substances from non-Norwalk virus-binding substances.

For in vivo applications, those skilled in the art will recognize that there are various known techniques to make non-human, e.g., mouse, monoclonal antibodies more compatible with human therapies, e.g., as described in Winter et al., *Nature,* 349:293–299, 1991; Sahagan et al., *J. Immunol.,* 137:1066–1074, 1986; and Boss et al., U.S. Pat. No. 4,816,397.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An assay to determine the presence of Norwalk virus or Norwalk virus antigens in a biological sample, the assay comprising the steps of
    contacting the sample with monoclonal antibody 1C9 or 1D8, which specifically binds to Norwalk virus particles from a naturally occurring Norwalk virus outbreak in human stool;
    reacting the sample and the monoclonal antibody for a time and under conditions that allow the formation of an immunocomplex between the monoclonal antibody and any Norwalk virus or virus antigens in the sample; and
    detecting the immunocomplex, the presence of the immunocomplex indicating the presence of human Norwalk virus or virus antigens in the sample.

2. The assay of claim 1, wherein the monoclonal antibody is 1C9.

3. The assay of claim 1, wherein the monoclonal antibody is 1D8.

4. An assay to determine the presence of Norwalk virus-specific IgM in a biological sample, the assay comprising the steps of
    isolating IgM in the sample;
    contacting the isolated IgM with purified Norwalk virus or Norwalk virus particles for a time and under conditions that allow the formation of a Norwalk virus-IgM complex between any Norwalk virus-specific IgM in the sample and the purified Norwalk virus or Norwalk virus particles;
    contacting the Norwalk virus-IgM complex with monoclonal antibody 1D8 or 1C9, which specifically binds to Norwalk virus particles from a naturally occurring Norwalk virus outbreak in human stool;
    reacting the complex and the monoclonal antibody for a time and under conditions that allow the formation of an immunocomplex between the monoclonal antibody and any Norwalk virus-IgM complexes; and detecting the immunocomplex, the presence of the immunocomplex indicating the presence of Norwalk virus-specific IgM in the sample.

5. The assay of claim 4, wherein the monoclonal antibody is 1C9.

6. The assay of claim 4, wherein the monoclonal antibody is 1D8.

7. A monoclonal antibody that specifically binds to a Norwalk virus antigen in stool from a human patient infected with Norwalk virus from a naturally occurring Norwalk virus outbreak, wherein the monoclonal antibody is 1C9.

8. A monoclonal antibody that specifically binds to a Norwalk virus antigen in stool from a human patient infected with Norwalk virus from a naturally occurring Norwalk virus outbreak, wherein the monoclonal antibody is 1D8.

9. An anti-idiotypic antibody that specifically binds to the monoclonal antibody of claim 7.

10. An anti-idiotypic antibody that specifically binds to the monoclonal antibody of claim 8.

11. A method of inducing an immunological response to Norwalk Virus, the method comprising:

(a) providing the anti-idiotypic antibody of claim 9 that binds to monoclonal antibodies directed against an epitope of the 58 kDa antigen of Norwalk Virus, and (b) stimulating in a mammal the production of anti-anti-idiotypic antibodies by administering to the mammal the anti-idiotypic antibody of claim 9.

12. A method of inducing an immunological response to Norwalk Virus, the method comprising:

(a) providing the anti-idiotypic antibody of claim 10 that binds to monoclonal antibodies directed against an epitope of the 58 kDa antigen of Norwalk Virus, and (b) stimulating in a mammal the production of anti-anti-idiotypic antibodies by administering to the mammal the anti-idiotypic antibody of claim 10.

* * * * *